(12) United States Patent
Getahoun

(10) Patent No.: US 8,372,381 B1
(45) Date of Patent: Feb. 12, 2013

(54) ACHIEVING LONG-TERM RELEASE OF HEALTH ENHANCING ELEMENTS FROM CHEMICAL COMPONENTS

(76) Inventor: Nebiyou Getahoun, Bethlehem, PA (US)

( * ) Notice: Subject to any disclaimer, the term of this patent is extended or adjusted under 35 U.S.C. 154(b) by 620 days.

(21) Appl. No.: 12/215,379

(22) Filed: Jun. 26, 2008

Related U.S. Application Data

(60) Provisional application No. 60/937,136, filed on Jun. 26, 2007.

(51) Int. Cl.
*A61K 9/68* (2006.01)
(52) U.S. Cl. ............... 424/48; 424/493; 426/3
(58) Field of Classification Search ............ 426/3
See application file for complete search history.

(56) References Cited

U.S. PATENT DOCUMENTS

2005/0042281 A1* 2/2005 Singh et al. ............ 424/464
2005/0175733 A1* 8/2005 Thorengaard et al. ........ 426/3

* cited by examiner

*Primary Examiner* — Darryl C Sutton
(74) *Attorney, Agent, or Firm* — Charles A. Wilkinson; Clinton H. Wilkinson

(57) ABSTRACT

A chewing gum carrier system for supplemental nutrients and pharmaceutical products is provided using compressed gum with a buffering system designed for simultaneous release and ultimate exhaustion of both flavor elements and supplementary nutritive elements and/or pharmacological values by use of a sodium carbonate, bicarbonate and magnesium oxide buffering system included in a compressed gum base, preferably using a plasticizer to prevent premature crumbling of the compressed gum base.

12 Claims, No Drawings

ACHIEVING LONG-TERM RELEASE OF HEALTH ENHANCING ELEMENTS FROM CHEMICAL COMPONENTS

RELATED APPLICATIONS

This application takes priority from U.S. Provisional Application 60/937,136 filed Jun. 26, 2007 by the present inventor under the same title.

BACKGROUND OF THE INVENTION

1. Field of the Invention

The present invention relates generally to the field of nutritional and dietary supplements and pharmaceutical products, and more particularly this invention relates to an improved release process for vitamins, active pharmaceutical products, flavoring systems, sweeteners and mineral supplements from a chewing gum-type carrying agent. Thus, the invention is in the field of improved release of flavor and nutritional elements from a chewable carrier or applicator composition over a controlled period. More particularly the present inventor provides an improved release system for vitamins and other health effecting elements for chewing gum-type applicator systems and the like.

2. Preliminary Discussion

Pharmaceutical and nutritional supplement dosage agents intended for oral administration are typically provided in solid form as tablets, capsules of various types, lozenges or so-called caplets or capsules. Tablets can be swallowed whole, usually with water, chewed in the mouth and then swallowed or sometimes applied sublingually, i.e. dissolved in the mouth, usually under the tongue. Absorption of the active moiety in the tablet depends upon its release from the dosage form, usually in a solid form, which may be controlled by various different technologies.

Since many consumers either dislike "taking pills" or may well forget to take them, attempts to encourage regular self-administration have been made by adding flavor elements to the pills or capsules.

More recently, the dosage of vitamin supplement elements and other pharmacological elements have been administered in the form of chewing gum. This has the advantage that the one taking the dosage will be more likely to take such dosage regularly and assuming they like to chew gum, or can be habituated to like it, will commonly take it regularly rather than regularly forgetting to take it. In addition, in the absence of a readily available water supply one can still take their vitamins or other supplemental nutritional elements or other medicine in the form of gum. while in pill form water is almost always required in order to aid in swallowing the supplement pill or in washing a chewed pill into the gastrointestinal tract.

It has been suggested previously, therefore, to provide dosages of supplemental vitamins of various kinds, as well as pharmacological elements such as nicotine, caffeine and other mild and unlikely to be abused pharmaceutical agents from chewable release agents such as chewing gum and the like together with flavor agents which encourage the user to continue chewing for the time necessary to obtain the desired dosage of the vitamins or other desired element.

Unfortunately, in such gum-type release systems, while there is an initial heavy release or flush of the substance desired to be released into the bucal and sublingual cavity, such release quickly declines or "drops off" so that the desired release substance such as a vitamin content and/or pharmaceutical content quickly declines along with the release of flavor content. While the rapid drop off or release of flavor or flavoring agent is not necessarily, at least in the eyes of many manufacturers, an undesirable effect, since it encourages the consumer of the chewing gum to discard the partially chewed gum and hopefully to take another or fresh piece of chewing gum, as a practical matter tests have shown that as much as 80 to 85% of any vitamins or other pharmaceutical elements remains in the gum element when it is discarded. Consequently, in a gum which advertises that it contains, for example, 200 units of vitamin B complex, 160 of such units will usually remain in the gum when such gum is discarded and as a result, the consumer is not provided with anywhere near, or anywhere like, the amount of vitamin content or other pharmaceutical contents which they believe they are receiving. This is not only a detriment to the consumer, but an unnecessary cost to the producer of the chewing gum release system or dosage system. Furthermore, assuming that the chewer is attempting to achieve a given dose of vitamins or other pharmaceutical unit, it is clearly necessary that they obtain most of the available content from each piece of gum chewed, since if the chewer believes they have to chew more gum to obtain the desired dosage, or aimed for dosage, they will have to chew more gum and may merely achieve an undesirable result.

Since many or, even most gum chewers will tend to throw away their gum and take another piece when the flavor element becomes exhausted, it is also desirable if the flavor element is substantially exhausted at the same time or at least not before the vitamin or pharmaceutical content is exhausted. It is also naturally desirable, so far as a manufacturer or vendor of the gum delivered pharmaceutical or supplement product is concerned, if the flavor element or enhancer does not last too long so that any given piece of product is not chewed too long in order to encourage the exchange for a new piece.

A fairly new gum technology, namely so-called compressed gum, has been commercialized in the last several years. Traditional gum has been made by essentially mixing together a viscoelastic component with any other desired ingredients such as flavor elements and the like including supplemental vitamins and/or pharmaceutical elements such as nicotine alkaloids and the like, with the mixing being conducted usually in steam jacketed mixers somewhat similar to large kitchen mixers and bowls or similar apparatuses. Because such mixing tends inherently to be uneven, or streaky, very similar to the mixing of cake or bread dough, such mixing has been at best uneven and in fact when such gums are chewed, additional mixing occurs in the mouth; but even then the flavor, pharmaceutical and buffering components are at best only partially mixed. This is satisfactory for some uses, but when one wishes the ingredients to be precisely released has been found to be less than satisfactory. Thus when the sticky gum material is extruded after initial mixing into usually a flat sheet which is then usually severed into thin strips which are then in turn severed into square or oblong sections of gum and forthwith wrapped, not only is the equipment covered with a sticky goo which requires a great deal of labor to clean and keep clean, but the mixing of ingredients in the gum is uneven at best and each piece, or stick, of gum varies considerably in the amount and distribution of any ingredients mixed into the gum or any portion of the gum. As a result, the coordination of a mixture of ingredients mixed together in the gum is invariably not very satisfactory.

The present inventor has found that by the use of the more recently commercially available technology of so-called compressed gum in which the gum components are initially formed into fine particles or particulates of powder which fine particles are then compressed by a tablet press into individual gum pieces of any desired shape or size that a much more satisfactory release system can be attained because the manufacturing process can be adapted to provide a much more intimate and accurate mixture of ingredients to provide a relatively accurate and uniform mix of ingredients in any particular gum particulate. The present inventor has also found that with the use of a precisely calculated amount of sweetening elements, nutritional supplement and/or pharmaceutical elements and buffing elements or substances all initially mixed together as fine particles or particulates together with the powdered gum particles or particulates and compressed together in a uniform larger particulate mass and then compressed into a final pellet or gum particle for consumption, a gum product can be and is produced which upon mastication in the mouth cavity will release both its nutritional supplement and/or pharmacological values at a precisely calculated rate usually designed to completely release both sweetening and nutritional and/or pharmaceutical moieties in a period of up to 30 minutes of mastication depending upon what is desired, or longer if desired, so that almost the full load of supplementary nutrition elements, or vitamins, are released during chewing or mastication followed immediately by a precipitous drop off of the sweetener released so that the average user will discard that particular piece of gum and select another piece. The individual component particles of the gum, flavor and nutritional and/or pharmacological elements are provided in a granulation fineness which will largely prevent any but very slight undesired reaction between them as long as kept dry to provide a desirable shelf life of several years, but will be finely enough divided so that an immediate release of such elements will occur in the bucal or mouth cavity upon mastication and exposure as a result of such mastication to moisture from the saliva of the mouth.

One characteristic of compressed gum that has proven unpopular with consumers is a tendency to feel that the gum is crumbling in the chewer's mouth until it has been significantly masticated, at which time it reverts to the feeling of typical gum. This feeling is caused by the fact that the gum particulates which are largely surrounded by other ingredients are in fact largely mechanically adhered by the pressure of the pelletizing process and because surrounded by other ingredients, initially break apart upon the beginning of mastication in the bucal cavity.

While such incipient crumbling is a benefit to expression or release of the other values for the gum, such as nutrients and pharmacological agents, its unfamiliar feeling of lack of consistency may be disconcerting to users of the gum products. Furthermore, crumbling will cause up to as much or more of the flavor and dietary supplement values to be almost immediately released followed by a tapering off period. The present inventor has found by extensive testing, however, that the use of a plasticiser during the manufacture of the final dose of compressed gum will alleviate the feeling of crumbling without seriously interfering with the expression of the nutritive content or pharmaceutical content of the compressed gum. Furthermore, the prevention of crumbling slows down the initial flush or release of ingredients and allows more exact control of simultaneous release of both the flavor and nutritive and pharmaceutical values by the proper use of buffers.

In order to have a proper effect, the plasticiser should be added to the formulation before a glidant material, i.e. silicon dioxide and lubricant are entered into or mixed into the formulation. By use of the plasticiser ingredient, the initial adherence of the gum particulates is increased and their breaking apart is delayed beyond the usual 30 seconds or so when the usual crumbling effect is noticeable after which the gum particulates are further driven together by the mastication itself. On the other hand, the release of the nutritional and/or pharmaceutical values are not substantially interfered with and less overall of such materials are necessary because they are not so much trapped in the gum, but completely expressed by proper buffering.

In order to obtain the desirable results of the invention, the present inventor has discovered that it is necessary to carefully balance the size and the amount of gum particles or particulates, flavor elements and release as well as buffering elements to obtain the desired simultaneous release of and ultimate exhaustion of flavor compounds, nutritional supplement compounds or elements and/or pharmacological compounds and release or buffering compound or compounds as well as plasticiser elements to provide the desired results and without such careful and critical combination the simultaneous release will not be obtained. By the broad term, nutritive values the invention includes not only various vitamin, agents, but also mineral nutritive agents, such as calcium, iron, zinc and the like.

Preferably non-nutritive sweetener compounds such as Xylitol, which is an alcohol rather than a sugar and does not normally support major bacterial activity in the mouth, is mixed in lesser amounts with aspartame and Ace-K which also do not readily support bacterial growth such as is found in the mouth or bucal cavity. At the same time, the buffering agents sodium carbonate and sodium bicarbonate are used in critical quantities and particular sizes to regulate the release of the flavor agents and supplemental nutritive values as well as any pharmacological values. Other release or buffering value agents could also be used such as magnesium stearate, potassium carbonate and citric acid can also have beneficial effects. None of these support bacterial activity and all but the citric acid tend to establish bucal cavity conditions that are not favorable to tooth decay.

3. Description of Related Art

British Patent 1,325,011 published Jul. 9, 1971 assigned to Aktiebolage Leo of Sweden contains a thorough discussion of the inclusion and release of so-called tobacco alkaloid or nicotine alkaloid from ordinary chewing gum. The disadvantage of too quick release is discussed and the use of ion exchange resin compositions and particularly cation exchangers designed to effect both retention and release of the nicotine alkaloid during chewing of the gum depending basically upon the acidity are discussed together with sweetening inclusions in the gum including both sugar based and sugarless based sweetening agents are discussed and the conditions for proper release of the nicotine alkaloid suggested. The release rate of the nicotine alkaloid from the gum composition is bound closely to the quantity of cation exchanger material, which is used, preferably in the hydrogen ionic form. Applicant's release system is not disclosed, however.

U.S. Pat. No. 5,637,313 issued Jun. 10, 1997 to Chau et al. discloses a method of making chewable dosage forms including the use of a gum base and various pharmaceutical agents and may include Xylitol, a sugarless sweetening agent in the form of an alcohol related to the sugar xylitose. A long list of possible inclusions is provided including modifiers, bulking agents and flavoring agents including calcium carbonate and the like. The applicant's particular composition, however, is not disclosed nor the applicant's method of making his product set forth.

U.S. Pat. No. 6,083,527 issued Jul. 4, 2000 to Thistle discloses the provision of a breath mint including particularly Xylitol as a natural sweetener buffered with calcium hydroxide to provide a confection to which vitamins may be added in dosage form. The simultaneous delivering of vitamins while preventing tooth decay because the ingredients do not encourage tooth decay is disclosed and the dosage vehicle is disclosed as including the use of a gum. Applicant's particular composition for attaining controlled release of both the flavoring and active ingredients is not disclosed, however.

U.S. Pat. No. 6,531,114 issued Mar. 11, 2003 to Gunder et al. assigned to the Wm. Wrigley, Jr. Company discloses the advantages of having a pharmacological sublingual or bucal route for certain pharmaceutical agents making absorption from a chewing gum vehicle particularly advantageous, but does not disclose the efficiency of compressed gum for gaining very immediate absorption in the mucus membranes of the bucal cavity.

U.S. Pat. No. 7,163,705 issued Jan. 16, 2007 to Johnson et al. and assigned to the Wm. Wrigley, Jr. Company thoroughly discusses the addition of various supplements and medicaments to the traditionally mixed gums with buffering systems comprised of sodium carbonate and sodium bicarbonate and includes a very large number of cited references. The use of compressed gum is not disclosed, however.

Rohm and Haas ion exchange product data sheet copyrighted in 2000 by Rohm and Haas Company provides a discussion of the use of Amberlite™ resin for controlled release of pharmacological units from compounds but does not disclose applicant's product or method of making.

OBJECTS OF THE INVENTION

It is an object of the present invention, therefore, to provide a nutritional or pharmaceutical dosage of an element from a gum-type carrier by a mechanism that assures that substantially the full content or charge of such dosage element will be expressed from the gum element during the normal chewing of such gum.

It is a still further object of the invention to provide a particularly effective carrier system for nutritional supplements.

It is a still further object of the invention to provide a release system for nutritional supplement and pharmacological values from a chewing gum type carrier in which the flavor elements, including in particular Xylitol and pharmaceutical values or nutritional supplement values are expressed substantially completely from the gum carrier during a given period of chewing of the gum carrier.

It is a still further object of the invention to make a chewing gum based carrier system for the treatment of nutritional and other conditions in which the flavor elements and nutritional and/or pharmacological elements are substantially completely expressed from, or given up by, the gum base during a predetermined interval of chewing of such gum base.

It is a still further object of the invention to provide a gum based carrier system based upon a compressed gum matrix containing predetermined amounts of flavor elements plus supplementary vitamins and/or pharmacological moieties buffered so that both such flavor elements will be released from the gum base within the same predetermined time interval with relative accuracy such that the supplementary nutritive values and flavor values will be exhausted at approximately the same time and the one using the gum base carrier will discard the gum base carrier at approximately the point at which the supplementary nutritive values and/or pharmaceutical values are fully expressed from the gum carrier.

It is a still further object of the invention to provide a gum carrier for expressing dietary nutritive supplement or pharmaceutical values to the bucal cavity or mouth cavity of the intended recipient of such values in which said gum carrier is a compressed gum base having an initial particle size such that 99.9% of the particles pass through a 2 mm. sieve, such carrier comprising a major portion of the final gum product and being internally mixed with a flavor element comprised of 50 to 80% Xylitol, plus Aspartame and Ace-K as a combined flavor moiety which does not support bacterial activity in the bucal cavity, plus an amount of a mixture of sodium carbonate and sodium bicarbonate as a buffer in an approximate ratio of between 0.01 to 0.1%, not including 0.1%, plus magnesium oxide from 0.01 to 2%, the remainder being supplementary vitamin values and/or pharmaceutical values plus magnesium sterate to control the consistency plus silicon dioxide as a glidant.

It is a still further object of the invention to provide a chewable dosage form for providing a release of supplementary vitamins from a gum base having a predetermined amount of flavor substances which are expressed during a predetermined interval of chewing during which substantially all of a content of a pharmacological moiety or moieties are expressed from the gum base.

It is therefore a still further object of the present invention to provide a compressible gum which contains a combination of both buffers and flavor and dietary supplement values (in different or same percent ratio and individually or in combination).

It is a still further object of the present invention to provide a buffer, which can control the release of sweetener. In this case (Xylitol in 50 to 80% level of the total sweetener).

It is a still further object of the present invention to provide a confection, which reduces bad breath (Xylitol in 50 to 80% level of the total sweetener).

It is a still further object of the present invention to provide a confection, which does not harm the teeth.

It is a still further object of the present invention to provide a confection, which enables one to enjoy a candy confection while simultaneously preventing tooth decay and bad breath, and taking their vitamins.

It is a still further object of the present invention to provide a method of manufacturing a confection, which confection prevents tooth decay and bad breath while administering vitamins.

It is a still further object of the invention to obtain particularly fast-acting pharmaceutical administration to the body via the use of compressed gum containing pharmaceuticals into the copious vascularization of the bucal cavity.

It is a still further object of the invention to provide a nutritive or pharmaceutical containing compressed gum containing a plasticiser agent to suppress an initial feeling of crumbling of a compressed gum capsule without serious interference with the expression of nutritive or pharmaceutical values simultaneously with taste elements from the gum.

Still other objects and advantages of the invention will become clear upon review of the following detailed description.

SUMMARY OF THE INVENTION

A chewable gum base of compressed gum particles is provided comprised of 80 to 96% gum particles having a particle size in which 99.9% of such particles pass through a 2 mm. sieve, the remainder being composed of between 50 and 80% Xylitol of the total sweeteners, the remainder being Aspartame and Ace-K plus a combination of sodium carbonate and sodium bicarbonate between 0.01 to 0.1, but not including 0.1%, plus magnesium oxide between 0.01 and 2.0% to appropriately buffer the flavor elements vitamin supplement levels and or pharmaceutical elements balanced such that the flavor elements and vitamin supplement content are substantially completely expressed from the gum base while the carrier gum is being chewed in the bucal cavity for approximately up to 30 minutes and are essentially completely expressed or exhausted from the gum base simultaneously so the dosage can be reasonably controlled, a plasticiser being added to the final gum particulate compression step to prevent "crumbling" of the compressed gum in the mouth. The administration of fast-acting pharmaceuticals via the bucal cavity and its copious vascularization is also improved by the use of a compressed gum vehicle for such drugs.

DETAILED DESCRIPTION OF THE PREFERRED EMBODIMENTS

The present invention relates generally to the field of Nutritional/Dietary supplements. More specifically, this invention relates to the release by a coordinated process of vitamins, a flavoring system, sweetener and mineral from directly compressed gum. Pharmaceutical moieties can be substituted for or used in combination with the vitamin moieties.

Pharmaceutical and nutritional supplement dosage forms intended for oral administration are typically provided in solid form as tablets capsules, pills, lozenges or caplets. The tablet form is swallowed whole, chewed in the mouth, or applied sublingually. Absorption of the active moiety depends upon its release from the dosage form and may be controlled by several different technologies.

The current invention very simply and effectively provides by the use of a buffer system (Sodium Carbonate and/or Sodium Bicarbonate plus Magnesium Oxide) very accurate control (the amount and the rate) of the release of vitamins, flavors, sweetener and pharmaceutical API from a compressed gum drug delivery system.

Chewable systems are advantageous where it is desirable to make an active ingredient available topically to the bucal or sublingual areas for both local effects or systemic absorption. Chewable dosage forms are often utilized to ease drug administration in children and geriatric patients.

Palatability and "mouth feel" are important characteristics to be considered in providing a dosage form, or matrix, for vitamins as well as active pharmaceutical products. By controlling the ratio and amount of buffer, in accordance with this invention it is possible to control the mouth feel as well as the expression of supplementary vitamin, mineral values or pharmaceutical values from a gum bar or piece of gum.

Each of the nutritional values such as vitamins and/or pharmaceutical values from a gum base coordinated with expression of taste elements is effected by the use not, only of compressed gum as a carrier, but also by the use of a plasticiser in a suitable range to prevent crumbling in the mouth of the compressed gum in combination with the use of a proper plasticiser.

By controlling the flavoring and sweetener system, one can improve the palatability of the compressed gum. By the same token, the slow release of the vitamin or other content will help better absorption via the bucal and sublingual cavity. This aspect of the invention results in less chance of such elements going straight to the gastrointestinal system, which is the case of some users, may cause stomach absenting.

The use of directly compressible gum as a delivery system (nutritional/dietary supplement) is fairly new. This excipient or bulk carrier can be used as a bucal/sublingual delivery system, however, only when it is used in the proper formula composition.

The present invention by the use of so-called direct compressed gum particularly with a suitable plasticiser together with an optimum release process provides very effective controlled release of flavor agents and supplements and pharmaceutical values at the same time. The advantage of this invention is that it helps to control the release process by changing the amount and ratio of sodium carbonate and/or sodium bicarbonate plus magnesium oxide in the overall formula, which in combination with the use of a compressed gum carrier provides quick and simultaneous release of nutrients and/or pharmaceutical values along with flavor elements. By the use of such control the advantages prolonging the release and achieving good palatability is attained Up to this point there has been no compressed gum delivery system, which utilizes this buffer system and suitable system to obtain the desired release profile because the dynamics of the delivery system have not been well understood.

In accordance with the invention, a given quantity of gum particulates designed for the formation of so-called compressed gum having a particle size in which 99.9% of the particles will pass through a 2 mm. screen, the more uniform the better, are placed in a dry state, in a dry mixer together additional materials of preferably similar granularity or particle size comprising 50 to 80% Xylitol, an alcohol compound which does not support bacterial growth and related to xylose or wood sugar made largely from hard wood chips, straw and the like plus preferably small amounts of aspartame and so-called Ace-K plus from 0.01 to 0.1% sodium carbonate and sodium bicarbonate and 0.1 to 2% magnesium oxide and as much of various vitamins such as $B_1$ through $B_{12}$, vitamins C, E, D, Beta Carotene multivitamins and any trace minerals such as calcium, iron and zinc as well as other nutritional trace minerals or may be replaced by pharmaceutical values or substances in dry form which are placed in the mixer with the granular gum particles and thoroughly mixed together, the gum particulates comprising from 80 to 96% of the whole. After thorough mixing together, the mixed ingredients are then compressed into tablets using a tablet press. A so-called glidant, namely very finely ground silicon dioxide and lubricant such as magnesium stearate, may be preferably added to the mix prior to placement in the pill compression apparatus to prevent tablet ejection problems, laminating and the like. In addition, in order to prevent detectable premature crumbling of the gum particulates in the bucal cavity during mastication, a quantity of a plasticiser is added to prevent crumbling of the compressed gum carrier, preferably added prior to the addition of the glidant and lubricant.

After compression, the thoroughly compressed gum conglomerate pieces or tablets will be found to be uniform and of a consistency which will hold together very effectively and as long as kept dry will have a very good shelf life of two years or more. However, when placed in the mouth, the gum pieces will be easily masticated and the various components mixed together with the gum particles will be released at a steady rate depending upon the amount of buffering material and initial plasticiser for a period of from 15 minutes to an hour or more and preferably about 20 minutes to half an hour. The more buffering materials, i.e. sodium carbonate and sodium bicarbonate plus magnesium oxide is used, the more rapidly will the flavor and other inclusions be released. While the use of such buffering agents has been known in normal gum, their importance in compressed gum systems has not been realized. Testing will reveal that both the flavor values and the nutritional supplement values of the final product or alternatively in some cases additionally pharmacological values will have been substantially completely expressed during the same period as the flavor values. This is due to the very even mixing of the gum particulates with the flavor and additional nutritive values with the buffer values resulting in a very controllable release over a desired period of the flavor elements and supplementary nutritive components or values and any pharmaceutical values, something which was unattainable as a practical matter before with the former processes for incorporating such values into gum mixed in the traditional way even with the most thorough mixing.

Since traditionally mixed gum products are mixed in an initially semi-liquid or viscoelastic form, the resulting shelf life tends to be less even if thereafter kept in a dry condition, because the use of traditional gummy gum in bulk which involves heating of the solid gum to convert into soft gum and the addition of liquid flavor at the fluent temperature results in the gum having some essentially liquid components in which it may start to degrade dry components in the gum product.

In the system of the invention, since the excipients are mixed with the compressed gum intra, i.e. outside of, rather than inter, i.e. within the gum particulates, the amount of the buffer required is comparatively small.

The buffers of the invention also enable the reduction of bacteria in the mouth and, thereby, the reduction of plaque, tooth decay and halitosis. The buffers of the present invention raise the overall pH level in the saliva in the mouth to make it more alkaline to provide an environment less conducive to bacterial growth which, in turn, reduces the rate of bacterial putrefaction of food debris and resultant tooth decay and the bad breath commonly associated therewith. Since the invention is in the form of a candy-like vitamin, it is very palatable to children. As a result of encouraging children to take the confection-type carrier of the present invention dental hygiene will be greatly facilitated, whereby by ingesting the "candy" of the present invention, children can automatically receive their vitamins while simultaneously increasing the pH level in their mouth to significantly reduce bacteria which cause tooth decay and bad breath.

The use of Xylitol in an amount of the total sweetener of 50 to 80% of the total sweetener can only be achieved due to the buffer system of the invention. Although only a lower level Xylitol is used, the gradual release of such sweetening agent helps to maintain the sweetening effect for a discrete predetermined period of time.

This invention involves use of a directly compressed gum upon the chewing of which will be changed into a viscoelastic substance. This solid but elastic material comprises confection, flavor agents, a glidant, and lubricant. The process of manufacturing involves an intimate mixing of vitamins with the sweetener, flavor and sodium carbonate and sodium bicarbonate. Then only the premix product will be mixed with the rest of ingredients.

The natural sweetener is preferably XYLITOL. The confectionery base is directly compressed gum and the flavoring may be natural or artificial flavoring, for example, mint flavoring, cinnamon, orange and fruit like flavoring, or almost any other flavoring desired.

In accordance with the invention, a very desirable compressed gum delivery system plus buffering system for a vitamin gum may comprise 80 to 96% of compressed gum particulates thoroughly mixed and dry compressed into tablets and containing in compressed particulate form 0.5 to 2% vitamin compounds, 0.2 to 3% liquid flavor elements, 0.5 to 3% magnesium stearate, 0.1-3% silicon dioxide, 0.1 to 2% aspartame, 0.2-2% Ace-K, 0.2 to 2% Xylitol, 0.01 to 0.1% sodium carbonate and 0.01 to 0.1% sodium bicarbonate, and 0.01 to 2% magnesium oxide plus 0.01 to 3% PEG plasticiser, the ingredients being coordinated to add up to 100% total ingredients. The buffers sodium carbonate, sodium bicarbonate and magnesium oxide as well as the plasticiser will be varied both in their absolute amounts and relative amounts dependent upon the time desired for full expression of both the flavor and sweetener elements from gum mastication by the user varying from a few minutes to a half hour or more. The relative amount of sodium carbonate and sodium bicarbonate buffer components can be varied depending upon the particular substances to be expressed from the system and the two or three buffering substances can in certain instances be used without the other for particular effects.

A suitable formulation of a dietary supplement gum in accordance with the present invention is in accordance with the present invention may be is as follows.

Compressed gum particulates ready to be mixed with other ingredients prior to compression in a gum tablet comprise 80 to 96% of the materials to be mixed with the remaining particulates defining the nature of the compressed gum tablet indicating all other ingredients in addition to compressed gum particulates comprising 4 to 20% of the total inclusive of the following:

|     |                     | Percent  |
| --- | ------------------- | -------- |
| (a) | Vitamins,           | 0.5-2.0  |
| (b) | Liquid Flavor,      | 0.2-3    |
| (c) | Solid Flavor,       | 0.5-10   |
| (d) | Magnesium Stearate, | 0.5-3    |
| (e) | Silicon Dioxide,    | 0.1-3    |
| (f) | Apartame,           | 0.1-2    |
| (g) | Ace-K.,             | 0.1-2    |
| (h) | Xylitol,            | 0.2-2    |
| (i) | Polyethylene Glycol | 0.01-3   |

Not only is the administration of nutritional supplements very useful through the use of compresses gum, but the administration of quick-acting pharmaceutical agents, such as, for example digitalis or various nitrates for angina, where quick absorption through the highly vasculated mucus membranes of the bucal cavity are natural materials for administration by a compressed gum vehicle where it is preferred that absorption be effected prior to the drug reaching the gastrointestinal tract.

The invention also provides a method for the interruption of formation of plaque through the manufacture of a solid breath-cleansing confection. This method comprises the steps of using an appropriate amount of natural sweetener which does not promote tooth decay to provide a sweetened; base containing flavoring; and thereby, create a natural sweetener containing a breath cleansing composition.

When manufacturing the breath cleansing and tooth decay prevention confection of the invention, the confection may further comprise other components such as sodium carbonate, sodium bicarbonate, magnesium stearate, used as the buffering medium which controls the expression of the sweeteners and flavoring values plus vitamin supplements values plus any pharmacological values.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

I claim:

1. A dietary supplement formula comprising:
   (a) a chewable gum base comprising compressed gum particles constituting 80 to 96% by weight of the whole,
   (b) a nutritional supplement formulation, comprising Vitamin B, Vitamin C, Vitamin E, Vitamin D, and Beta Carotene in an amount of 0.5-2%,
   (c) sweetener in an amount of 0.1-4%,
   (d) a buffer system for controlling the amount and rate of release of said nutritional supplement formulation and said sweetener wherein at least two of the following buffers are present in appropriate concentrations; sodium carbonate in an amount of between 0.01% and up to but not including 0.1% by weight of the whole, sodium bicarbonate in an amount of between 0.01 and up to but not including 0.1% by weight of the whole, and magnesium oxide in an amount of between 0.01 and 2% by weight of the whole, and
   (e) PEG plasticizer in an amount of 0.01 to 5% of the compressed gum ingredients,
when said dietary supplement formula is chewed the nutritional supplement formulation and the sweetener are released from the gum base within the same predetermined time interval.

2. A dietary supplement formula in accordance with claim 1 additionally comprising a mineral supplement formulation.

3. A dietary supplement formula in accordance with claim 1 further comprising:
   0.2-3% flavoring, 0.5-3% lubricant, and 0.1-3% glidant.

4. A dietary supplement formula in accordance with claim 3 in which the buffer system is comprised of about 0.01 to about 0.1% sodium carbonate.

5. A dietary supplement formula in accordance with claim 3 in which the buffer system is comprised of about 0.01 to about 0.1% sodium bicarbonate.

6. A dietary supplement formula in accordance with claim 3 in which the buffer system is comprised of about 0.01 to about 0.2% magnesium oxide.

7. A dietary supplement in accordance with claim 3 additionally containing an herbal extract.

8. A dietary supplement in accordance with claim 3 in which the PEG plasticiser is added before the glidant and lubricant are added to the formula.

9. A dietary supplement formulation in accordance with claim 3 in which the flavoring comprises a liquid flavor and solid flavor.

10. A dietary supplement formulation in accordance with claim 3 in which the lubricant comprises Magnesium stearate.

11. A dietary supplement formulation in accordance with claim 3 in which the glidant comprises Silicon Dioxide.

12. A dietary supplement formulation in accordance with claim 3 in which the sweetener comprises Aspartame and Ace-K.

* * * * *